US011873712B2

United States Patent
Song et al.

(10) Patent No.: US 11,873,712 B2
(45) Date of Patent: Jan. 16, 2024

(54) EDGE AND BOTTOM WATER INVASION SIMULATION APPARATUS AND METHOD FOR GAS RESERVOIR, STORAGE MEDIUM, AND PRODUCT

(71) Applicant: China University of Petroleum-Beijing, Beijing (CN)

(72) Inventors: Zhaojie Song, Beijing (CN); Changxiao Cao, Beijing (CN); Daqian Zeng, Beijing (CN); Shaohua Gu, Beijing (CN); Jiangbo Dong, Beijing (CN); Rui Zhang, Beijing (CN); Zehui Xie, Beijing (CN); Ying Jia, Beijing (CN)

(73) Assignee: China University of Petroleum—Beijing, Beijing (CN)

( * ) Notice: Subject to any disclaimer, the term of this patent is extended or adjusted under 35 U.S.C. 154(b) by 293 days.

(21) Appl. No.: 17/495,640

(22) Filed: Oct. 6, 2021

(65) Prior Publication Data

US 2023/0021874 A1 Jan. 26, 2023

(30) Foreign Application Priority Data

Jul. 23, 2021 (CN) .......................... 202110839749.5

(51) Int. Cl.
*E21B 49/00* (2006.01)
*E21B 41/00* (2006.01)
(Continued)

(52) U.S. Cl.
CPC .............. *E21B 49/00* (2013.01); *E21B 41/00* (2013.01); *E21B 43/12* (2013.01); *E21B 47/00* (2013.01);
(Continued)

(58) Field of Classification Search
CPC .......... E21B 41/00; E21B 43/12; E21B 47/00; E21B 49/00; G01N 33/241; G09B 25/02
See application file for complete search history.

(56) References Cited

U.S. PATENT DOCUMENTS 5,299,453 A * 4/1994 Sprunt ............... G01N 15/0893
73/152.23
9,790,743 B2 * 10/2017 Li ........................... E21B 34/00
(Continued)

FOREIGN PATENT DOCUMENTS

CN 104141490 A 11/2014
CN 108505987 A * 9/2018 ............. E21B 47/00
(Continued)

OTHER PUBLICATIONS

Yuliang Zhou et al., Experiment on Water Invasion in Shale Sequence during Gas Drilling Process, Natural Gas Geoscience, Oct. 2011, vol. 22, No. 5, China Academic Journal Electronic Publishing House, http://www.cnki.net, China (English abstract provided).

(Continued)

*Primary Examiner* — Jill E Culler
(74) *Attorney, Agent, or Firm* — Pokalsky Wilczynski Brozek, LLP (57) ABSTRACT

The present disclosure provides an edge and bottom water invasion simulation apparatus and method, a storage medium, and a product. A controller controls an inert gas to be injected into a first intermediate container, and stops the injection. The controller controls formation water to be injected into the first intermediate container, and stops the injection. The controller controls the first intermediate container to be communicated with a core holder, and adjusts a pressure of a back pressure valve, so that the formation water enters a core to simulate edge and bottom water invasion. In the present disclosure, by adding the inert gas (Continued)

and the formation water to the intermediate container, an infinite edge and bottom water with sufficient energy at an early stage of a water invasion and a limited edge and bottom water with lower energy at a later stage of the water invasion can be effectively simulated.

11 Claims, 6 Drawing Sheets

(51) Int. Cl.
*G01N 33/24* (2006.01)
*G09B 25/02* (2006.01)
*E21B 43/12* (2006.01)
*E21B 47/00* (2012.01)
*G06F 30/20* (2020.01)
*G06F 111/10* (2020.01)

(52) U.S. Cl.
CPC ........... *G01N 33/241* (2013.01); *G09B 25/02* (2013.01); *E21B 2200/20* (2020.05); *G06F 30/20* (2020.01); *G06F 2111/10* (2020.01)

(56) References Cited

U.S. PATENT DOCUMENTS

| | | | |
|---|---|---|---|
| 10,767,428 B2 * | 9/2020 | Yang | ........................ E21B 21/08 |
| 10,876,397 B2 * | 12/2020 | Yang | ........................ E21B 21/08 |
| 2016/0357888 A1 | 12/2016 | Li | |
| 2020/0056477 A1 * | 2/2020 | Yang | ........................ E21B 21/01 |

FOREIGN PATENT DOCUMENTS

| | | | |
|---|---|---|---|
| CN | 108505987 A | | 9/2018 |
| CN | 109307755 A | | 2/2019 |
| CN | 111021976 A | | 4/2020 |
| CN | 112082945 A | * | 12/2020 |
| CN | 112082945 A | | 12/2020 |

OTHER PUBLICATIONS

First Office Action dated Nov. 16, 2022, in priority application CN 202110839749.5.

* cited by examiner

EDGE AND BOTTOM WATER INVASION SIMULATION APPARATUS AND METHOD FOR GAS RESERVOIR, STORAGE MEDIUM, AND PRODUCT

CROSS-REFERENCE TO RELATED APPLICATION

This application claims priority to Chinese Patent Application No. 202110839749.5, filed on Jul. 23, 2021, which is hereby incorporated by reference in its entirety.

TECHNICAL FIELD

The present disclosure relates to the field of gas reservoir development technologies, and in particular, to an edge and bottom water invasion simulation apparatus and method for gas reservoir, a storage medium, and a product.

BACKGROUND

During natural gas exploration and development, when active edge and bottom water are present a gas reservoir, a risk of water invasion exists in the exploitation process. Once the water invasion occurs in the gas reservoir, on one hand, a gas and water two-phase seepage is formed in the gas reservoir, so that an ability of the gas-phase seepage is reduced, and a productivity of a single well is rapidly reduced. On another hand, the water invasion can trap a large amount of gas in modes of blocking, bypassing, water locking, or the like, so that a recovery of the gas reservoir is reduced.

In existing simulation experiments of the edge and bottom water invasion, a constant pressure method or a constant volume method is often used for simulating the edge and bottom water of the gas reservoir. The constant pressure method is used for simulating infinite edge and bottom water with sufficient energy, and a piston container is displaced by a constant pressure pump, and the edge and bottom water floods in a core at a constant pressure. The constant volume method is often used for simulating limited edge and bottom water with lower energy, and the edge and bottom water flows into the core spontaneously with expansion energy of the water per se as a driving force.

SUMMARY

The present disclosure provides an edge and bottom water invasion simulation apparatus and method for gas reservoir, a storage medium, and a product, so as to solve the problem that the infinite edge and bottom water with sufficient energy and the limited edge and bottom water with lower energy cannot be simulated in the same water invasion experiment.

In a first aspect, the present disclosure provides an edge and bottom water invasion simulation apparatus, including:
a first intermediate container, a core holder, a back pressure valve, and a controller, where a first piston is disposed in the first intermediate container, and the first piston is configured to separate formation water and an inert gas; a liquid outlet end of the first intermediate container is connected to an inlet end of the core holder, and an outlet end of the core holder is connected to the back pressure valve; the controller is connected to the first intermediate container, the core holder, and the back pressure valve, respectively;
the controller is configured to control the inert gas to be injected into the first intermediate container through a gas inlet end of the first intermediate container, and to stop the inert gas from being injected into the first intermediate container when an internal pressure of the first intermediate container reaches an initial gas pressure;
the controller is configured to control the formation water to be injected into the first intermediate container through a liquid inlet end of the first intermediate container, and to stop the formation water from being injected into the first intermediate container when the internal pressure of the first intermediate container reaches an initial formation pressure;
the controller is configured to control the liquid outlet end of the first intermediate container to be communicated with the inlet end of the core holder;
the controller is configured to adjust a pressure of the back pressure valve to reduce a pressure at the outlet end of the core holder, so that the formation water in the first intermediate container flows into a core in the core holder through the liquid outlet end of the first intermediate container and the inlet end of the core holder sequentially, so as to simulate an edge and bottom water invasion.

In a second aspect, the present disclosure provides an edge and bottom water invasion simulation method, including:
determining an initial gas pressure according to an actual recovery of natural gas, controlling an inert gas to be injected into a first intermediate container through a gas inlet end of the first intermediate container, and stopping the inert gas from being injected into the first intermediate container when an internal pressure of the first intermediate container reaches the initial gas pressure;
controlling formation water to be injected into the first intermediate container through a liquid inlet end of the first intermediate container, and stopping the formation water from being injected into the first intermediate container when the internal pressure of the first intermediate container reaches an initial formation pressure; and
controlling a liquid outlet end of the first intermediate container to be communicated with an inlet end of a core holder, and adjusting a pressure of a back pressure valve to reduce a pressure at an outlet end of the core holder, so that the formation water in the first intermediate container enters a core saturated with the natural gas in the core holder through the liquid outlet end of the first intermediate container and the inlet end of the core holder sequentially, so as to simulate an actual edge and bottom water invasion.

In a third aspect, an embodiment of the present disclosure provides a non-transitory computer-readable storage medium. Computer-executable instructions are stored in the computer-readable storage medium, and when a processor executes the computer-executable instructions, the method as described in the second aspect is implemented.

In a fourth aspect, an embodiment of the present disclosure provides a computer program product, including computer programs. When a processor executes the computer programs, the method as described in the second aspect is implemented.

In an edge and bottom water invasion simulation apparatus and method, a storage medium and a product provided by the present disclosure, the first intermediate container is disposed in the edge and bottom water invasion simulation apparatus, the first piston is disposed in the first intermediate container, and the first piston is configured to separate the formation water and the inert gas. The controller controls the inert gas to enter the first intermediate container, and stops the injection of the inert gas when the internal pressure of the first intermediate container reaches the initial gas pressure. The controller controls the formation water to be injected into the first intermediate container, and stops the injection of the formation water when the internal pressure of the first intermediate container reaches the initial formation pressure, and controls the liquid outlet end of the first intermediate container to be communicated with the inlet end of the core holder, and adjusts the pressure of the back pressure valve to reduce the pressure at the outlet end of the core holder, so that the formation water in the first intermediate container enters the core in the core holder, so as to simulate the edge and bottom water invasion. Since gas is easier to be compressed compared to water, by adding the inert gas and the formation water to the first intermediate container, the infinite edge and bottom water with sufficient energy at the early stage of the water invasion and the limited edge and bottom water with lower energy at the later stage of the water invasion can be effectively simulated.

BRIEF DESCRIPTION OF DRAWINGS

Accompanying drawings herein are incorporated into the description and constitute a part of the description. The drawings show embodiments in accordance with the present disclosure, and together with the description, are used to explain the principle of the present disclosure.

DESCRIPTION OF REFERENCE NUMERALS

10—First intermediate container; 11—Core holder; 12—Back pressure valve;
13—First piston; 14—Second intermediate container; 15—Second piston;
16—Displacement pump; 17—Third intermediate container; 18—Third piston;
19—Gas-liquid separator; 20—Gas flow meter; 21—Valve;
22—Pressure gauge.

The above drawings show the specific embodiments of the present disclosure, which will be described in more detail below. These drawings and text descriptions are not intended to limit the scope of the concept of the present disclosure in any way, but to describe the concept of the present disclosure for those skilled in the art with reference to the specific embodiments.

DESCRIPTION OF EMBODIMENTS

Exemplary embodiments will be described in detail here, and examples thereof are shown in the accompanying drawings. When the following description refers to the drawings, unless otherwise indicated, the same numbers in different drawings indicate the same or similar elements. The implementation manners described in the following exemplary embodiments do not represent all implementation manners consistent with the present disclosure, but are merely examples of apparatuses and methods consistent with some aspects of the present disclosure as detailed in the appended claims.

In order to clearly understand technical solutions of the present disclosure, solutions in the prior art will be introduced firstly in detail.

In the prior art, in edge and bottom water invasion simulation experiments, experimental apparatuses such as an intermediate container containing water and a core holder are used for simulating an edge and bottom water invasion, and the constant pressure method or the constant volume method is usually used for simulating the edge and bottom water of the gas reservoir. The constant pressure method is used for simulating the infinite edge and bottom water with sufficient energy, and the piston container is displaced by the constant pressure pump, and the water in the intermediate container is driven into a core in a core holder at a constant pressure. The constant volume method is often used for simulating the limited edge and bottom water with lower energy, and the water in the intermediate container flows into the core in the core holder spontaneously with the expansion energy of the water per se as the driving force.

In existing simulation experiments, in an actual water invasion of the gas reservoir, at the early stage of the water invasion, the edge and bottom water has sufficient energy, which is similar to the infinite edge and bottom water with sufficient energy, but as the development progresses, an overall pressure of the gas reservoir reduces, and the edge and bottom water has gradually exhausted energy, which is similar to the limited edge and bottom water with lower energy. When different waters are simulated, different methods are used, and the infinite edge and bottom water with sufficient energy and the limited edge and bottom water with lower energy cannot be simulated in the same water invasion experiment in the prior art.

Therefore, in view of the problem in the prior art that the infinite edge and bottom water with sufficient energy and the limited edge and bottom water with lower energy cannot be simulated in the same water invasion experiment, the inventors found in the research that a piston is provided in an intermediate container, and the piston is configured to separate formation water and an inert gas, a controller controls the inert gas to enter the intermediate container, and stops the injection of the inert gas when an internal pressure of the intermediate container reaches an initial gas pressure, the controller controls the formation water to be injected into the intermediate container, and stops the injection of the formation water when the internal pressure of the first intermediate container reaches an initial formation pressure, and controls a liquid outlet end of the intermediate container to be communicated with an inlet end of a core holder, and adjusts a pressure of a back pressure valve to reduce a pressure at an outlet end of the core holder, so that the formation water in the intermediate container enters a core in the core holder, so as to simulate an edge and bottom water invasion. By adding the inert gas and the formation water to the intermediate container, the infinite edge and bottom water with sufficient energy at the early stage of the water invasion and the limited edge and bottom water with lower energy at the later stage of the water invasion can be effectively simulated.

Therefore, the inventors propose the technical solutions of the embodiments of the present disclosure based on the above creative discovery.

Embodiment 1

Figure 1:
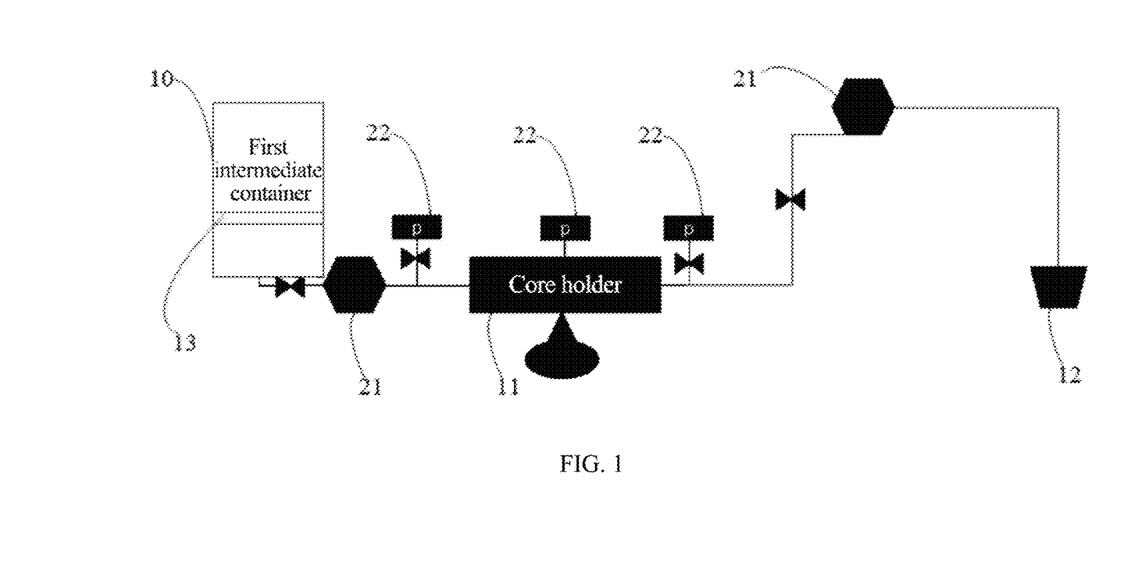
FIG. 1 is a schematic structural diagram of an edge and bottom water invasion simulation apparatus according to Embodiment 1 of the present disclosure.

FIG. 1 is a schematic structural diagram of an edge and bottom water invasion simulation apparatus according to Embodiment 1 of the present disclosure.

The edge and bottom water invasion simulation apparatus according to the present disclosure includes a first intermediate container 10, a core holder 11, a back pressure valve 12, and a controller. A first piston 13 is disposed in the first intermediate container 10, and the first piston 13 is configured to separate formation water and an inert gas. A liquid outlet end of the first intermediate container 10 is connected to an inlet end of the core holder 11, and an outlet end of the core holder 11 is connected to the back pressure valve 12. The controller is connected to the first intermediate container 10, the core holder 11, and the back pressure valve 12, respectively. The controller is configured to control the inert gas to be injected into the first intermediate container 10 through a gas inlet end of the first intermediate container 10, and to stop the inert gas from being injected into the first intermediate container 10 when an internal pressure of the first intermediate container 10 reaches an initial gas pressure. The controller is configured to control the formation water to be injected into the first intermediate container 10 through a liquid inlet end of the first intermediate container 10, and to stop the formation water from being injected into the first intermediate container 10 when the internal pressure of the first intermediate container 10 reaches an initial formation pressure. The controller is configured to control the liquid outlet end of the first intermediate container 10 to be communicated with the inlet end of the core holder 11. The controller is configured to adjust a pressure of the back pressure valve 12 to reduce a pressure at the outlet end of the core holder 11, so that the formation water in the first intermediate container 10 enters a core in the core holder 11 through the liquid outlet end of the first intermediate container 10 and the inlet end of the core holder 11 sequentially, so as to simulate an edge and bottom water invasion.

Referring to FIG. 1, the edge and bottom water invasion simulation apparatus includes the first intermediate container 10, the core holder 11, the back pressure valve 12, and the controller (not shown in FIG. 1). The first intermediate container 10 is a piston-type intermediate container, and is provided with the first piston 13 therein. The first piston 13 is configured to separate the inert gas and the formation water. The first piston 13 can move up and down in the first intermediate container when it is extruded.

The first intermediate container 10 includes a gas inlet end, a gas outlet end, the liquid inlet end, and the liquid outlet end. The gas inlet end of the first intermediate container 10 is connected to an inert gas storage tank (not shown in FIG. 1). The gas outlet end of the first intermediate container 10 is connected to an inert gas storage tank (not shown in FIG. 1) or a waste gas tank (not shown in FIG. 1). The liquid inlet end of the first intermediate container 10 is connected to a formation water storage tank (not shown in FIG. 1), and the liquid outlet end of the first intermediate container 10 is connected to the inlet end of the core holder 11.

The core holder 11 includes the inlet end, the outlet end, a core holding barrel, and a confining pressure device, or the like. The core holding barrel is configured to place the core. The outlet end of the core holder 11 is connected to the back pressure valve 12, the back pressure valve 12 is connected to a gas-liquid separator (not shown in FIG. 1), and the gas-liquid separator is connected to a gas flow meter (not shown in FIG. 1).

The controller is connected to the first intermediate container 10, the core holder 11, the back pressure valve 12, the gas-liquid separator, and the gas flow meter, respectively. As shown in FIG. 1, the edge and bottom water invasion simulation apparatus further includes a plurality of pressure gauges 22, and the controller is connected to the plurality of pressure gauges 22, respectively. One of the pressure gauges 22 is used to read the internal pressure of the first intermediate container 10, one of the pressure gauges 22 is used to read a pressure at the inlet end of the core holder 11, one of the pressure gauges 22 is used to read the pressure at the outlet end of the core holder 11, and one of the pressure gauges 22 is used to read an internal pressure of the core holder 11. The edge and bottom water invasion simulation apparatus further includes a plurality of valves 21, and the above components are connected to each other through the valves 21 and pipes.

After the controller receives an edge and bottom water invasion simulation instruction, the controller can control the inert gas in the inert gas storage tank to enter an upper part of the first intermediate container 10 through the gas inlet end of the first intermediate container 10, detect the internal pressure of the first intermediate container 10, and stop the inert gas from being injected into the first intermediate container 10 when the internal pressure of the first intermediate container 10 reaches the initial gas pressure. After that, the formation water needs to be injected into the first intermediate container 10, and the controller further controls the formation water in the formation water storage tank to enter a lower part of the first intermediate container 10 through the liquid inlet end of the first intermediate container 10. The formation water enters the first intermediate container 10, and then pushes the first piston to move upward to compress the inert gas in the upper part of the first intermediate container 10. The internal pressure of the first intermediate container 10 is detected, and the injection of the formation water into the first intermediate container 10 is stopped when the internal pressure of the first intermediate container 10 reaches the initial formation pressure. The initial formation pressure can be set according to actual situations. In actual natural gas exploitation, an initial formation pressure during non-exploitation will be measured in advance. In order to restore an actual exploitation environment, the initial formation pressure can be set to the corresponding initial formation pressure during non-exploitation of the formation. The initial formation pressure can also be set according to user's needs.

The controller controls the liquid outlet end of the first intermediate container 10 to be communicated with the inlet end of the core holder 11. At this time, the core in the core holder 11 is in a saturated state, that is, the core is a core saturated with natural gas. The internal pressure of the core holder 11 is the initial formation pressure, that is, the internal pressure of the core holder 11 is equal to the internal pressure of the first intermediate container 10 at this time. The controller adjusts the pressure of the back pressure valve 12 to reduce the pressure at the outlet end of the core holder 11, and the pressure at the outlet end of the core holder 11 is lower than the internal pressure of the core holder 11, so that the natural gas in the core flows out from the outlet end of the core holder 11, and a reduction in the internal pressure of the core holder 11 causes the formation water in the first intermediate container 10 to enter the core in the core holder 11 through the liquid outlet end of the first intermediate container 10 and the inlet end of the core holder 11 sequentially, thereby simulating the edge and bottom water invasion. As the formation water in the first intermediate container 10 flows out, the internal pressure of the first intermediate container 10 is reduced, so that the inert gas in the upper part of the first intermediate container 10 expands. According to the principle of gas decompression and expansion, an expansion volume of the inert gas in the upper part of the first intermediate container 10 is equal to a discharge volume of the formation water in the lower part. By combining with equation of state of gas and core parameters, a water invasion volume in the core can be quantitatively controlled, so that water breakthrough time of the outlet end of the core holder 11 and a recovery of the natural gas during the water breakthrough are consistent with those in the actual exploitation, thereby accurately simulating the actual exploitation process. By adding the inert gas and the formation water to the first intermediate container, the infinite edge and bottom water with sufficient energy at the early stage of the water invasion and the limited edge and bottom water with lower energy at the later stage of the water invasion can be effectively simulated.

Embodiment 2

Figure 2:
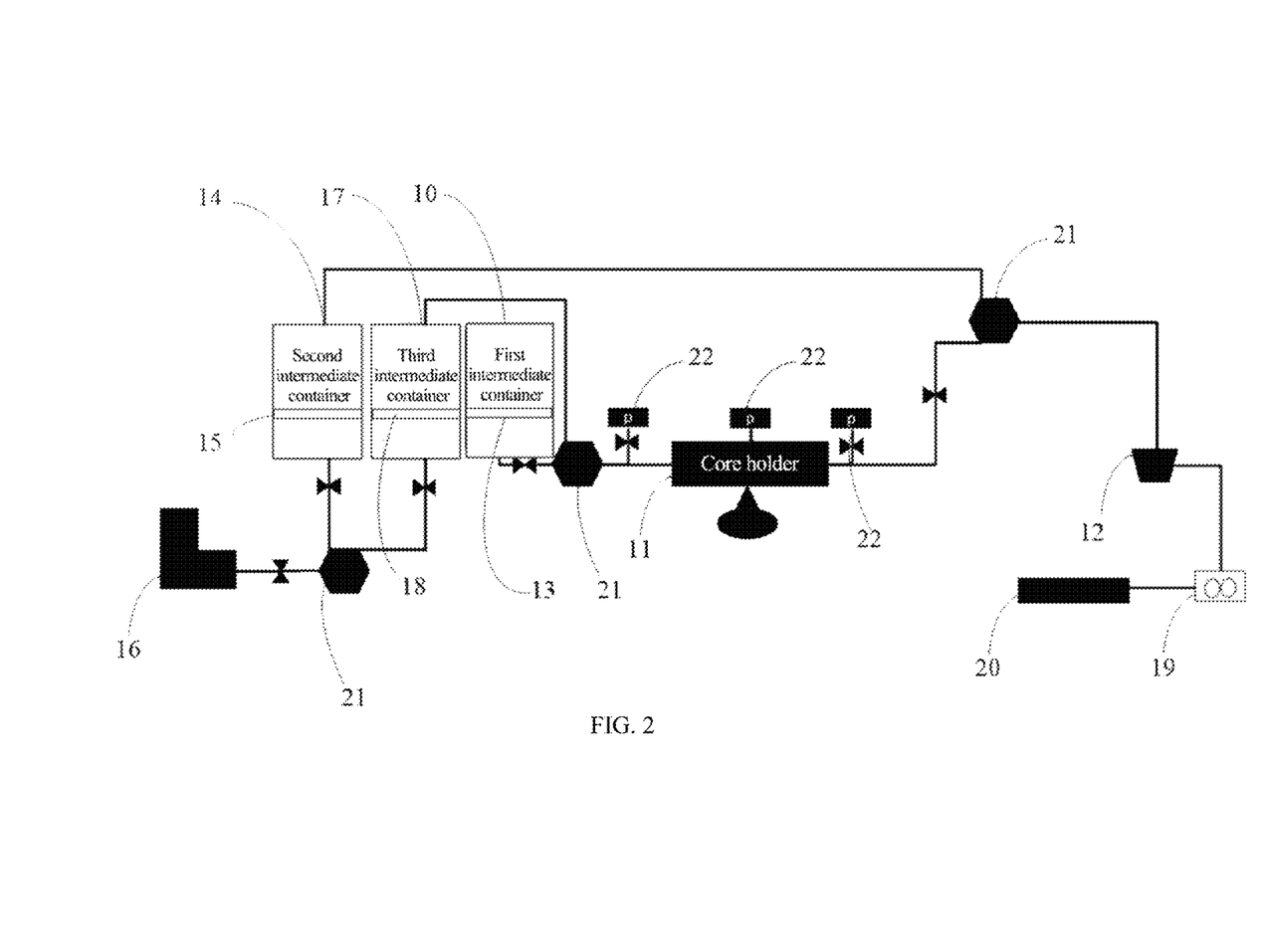
FIG. 2 is a schematic structural diagram of an edge and bottom water invasion simulation apparatus according to Embodiment 2 of the present disclosure.

FIG. 2 is a schematic structural diagram of an edge and bottom water invasion simulation apparatus according to Embodiment 2 of the present disclosure.

Optionally, the edge and bottom water invasion simulation apparatus further includes a second intermediate container 14, a displacement pump 16, and a recovery device. A second piston 15 is disposed in the second intermediate container 14, and the second piston 15 is configured to separate an inert gas and a liquid. The second intermediate container 14 is connected to the displacement pump 16, a gas outlet end of the second intermediate container 14 is connected to the outlet end of the core holder 11, and the outlet end of the core holder 11 is connected to the recovery device. The controller is connected to the second intermediate container 14, the displacement pump 16, and the recovery device, respectively. The controller is further configured to control the outlet end of the core holder 11 to be disconnected from the recovery device when the outlet end of the core holder 11 is subjected to a first water breakthrough. The controller is further configured to set a corresponding pressure value of the displacement pump 16 to the initial formation pressure, so that the liquid enters the second intermediate container 14 from a liquid inlet end of the second intermediate container 14 to compress the inert gas in the second intermediate container, so as to make an internal pressure of the second intermediate container 14 reach the initial formation pressure. The controller is further configured to, when the internal pressure of the second intermediate container 14 reaches the initial formation pressure, control the outlet end of the core holder to be communicated with the gas outlet end of the second intermediate container 14, so that the inert gas in the second intermediate container 14 enters the core holder 11 through the gas outlet end of the second intermediate container 14 and the outlet end of the core holder sequentially. The controller is further configured to determine an injection volume of the inert gas entering the core holder 11 according to a liquid injection volume when the internal pressure of the core holder 11 reaches the initial formation pressure. The controller is further configured to, when the internal pressure of the core holder 11 reaches the initial formation pressure, control the outlet end of the core holder 11 to be communicated with the recovery device, and adjust the pressure of the back pressure valve 12 to reduce the pressure at the outlet end of the core holder 11, so that a gas inside the core holder 11 flows from the outlet end of the core holder 11 into the recovery device. The controller is further configured to, when the outlet end of the core holder 11 is subjected to a second water breakthrough, control the outlet end of the core holder 11 to be disconnected from the recovery device, and analyze the components of the gas recovered by the recovery device to determine a recovery volume of the natural gas, and determine a recovery of the natural gas during the second water breakthrough according to the recovery volume of the natural gas and a total volume of the natural gas in the core saturated with the natural gas.

In this embodiment, the edge and bottom water invasion simulation apparatus further includes the second intermediate container 14, the displacement pump 16, and the recovery device (not shown in FIG. 2). The second piston is disposed in the second intermediate container 14, and the second piston is configured to separate the inert gas and the liquid. The second intermediate container 14 is connected to the displacement pump 16, and the displacement pump 16 is configured to displace the liquid.

The second intermediate container 14 includes a gas inlet end, the gas outlet end, the liquid inlet end, and a liquid outlet end. The gas inlet end of the second intermediate container 14 is connected to an inert gas storage tank, and the gas outlet end of the second intermediate container 14 is connected to the outlet end of the core holder 11. The gas outlet end of the second intermediate container 14 may further be connected to an inert gas storage tank or a waste gas tank. The liquid inlet end of the second intermediate container 14 is connected to a liquid storage tank, and the liquid outlet end of the second intermediate container 14 is connected to a liquid storage tank or a waste liquid tank. The displacement pump 16 is configured to displace the liquid, and to introduce a liquid contained in the liquid storage tank into the second intermediate container 14. The recovery device is connected to the outlet end of the core holder 11 for collecting gas. The controller is connected to the second intermediate container 14, the displacement pump 16, and the recovery device, respectively.

In this embodiment, when the outlet end of the core holder 11 is subjected to the first water breakthrough, since the outlet end of the core holder 11 no longer produces gas, the controller controls the outlet end of the core holder to be disconnected from the recovery device, and the recovery is stopped. There is still remaining natural gas in the core that has not been produced. Further, the inert gas can be used to push the formation water in, and then the recovery is performed. Specifically, the controller sets the displacement pump 16 to be in a constant pressure mode, and the pressure value is the initial formation pressure, so that the liquid contained in the liquid storage tank is introduced into the second intermediate container 14. The liquid enters the second intermediate container 14, and then pushes the second piston to move upward to compress the inert gas in an upper part of the second intermediate container 14, so that the internal pressure of the second intermediate container 14 reaches the initial formation pressure. According to a liquid intake amount of the liquid entering the second intermediate container 14 and a volume of the inert gas in the second intermediate container 14, a volume of the inert gas of high pressure can be calculated.

In this embodiment, after the internal pressure of the second intermediate container 14 reaches the initial formation pressure, the controller controls the outlet end of the core holder 11 to be communicated with the gas outlet end of the second intermediate container 14. Since the pressure at the outlet end of the core holder 11 is less than the internal pressure of the second intermediate container 14, the inert gas in the second intermediate container 14 enters the core holder 11 through the gas outlet end of the second intermediate container 14 and the outlet end of the core holder 11 sequentially. Until the internal pressure of the core holder 11 reaches the initial formation pressure, the injection of the inert gas into the core holder 11 is stopped. At this time, a liquid intake amount of the displacement pump 16 is obtained, and the liquid intake amount of the displacement pump 16 is equal to the injection volume of the inert gas injected into the core holder 11. In addition, when the internal pressure of the core holder 11 reaches the initial formation pressure, the recovery can be performed at this time, and the controller controls the outlet end of the core holder 11 to be communicated with the recovery device. Further, a gas is discharged from the outlet end of the core holder 11, and the gas includes the inert gas and the natural gas. Then, when the outlet end of the core holder 11 is subjected to the second water breakthrough, the outlet end of the core holder 11 is controlled to be disconnected from the recovery device, and the recovery is not performed.

Optionally, the edge and bottom water invasion simulation apparatus further includes the gas-liquid separator 19 and the gas flow meter 20. The gas-liquid separator 19 can be used to separate a liquid and a gas at the outlet end of the core holder 11, and the gas flow meter 20 is used to record an amount of a gas produced at the outlet end of the core holder 11. The edge and bottom water invasion simulation apparatus further includes a gas chromatograph, and the gas chromatograph is controlled to analyze the gas recovered by the recovery device, so as to determine the recovery volume of the natural gas. The recovery of the natural gas during the second water breakthrough is determined according to the recovery volume of the natural gas and the total volume of the natural gas in the core saturated with the natural gas. Specifically, a ratio of the recovery volume of the natural gas to the total volume of the natural gas in the core saturated with the natural gas is calculated, and the ratio is determined as the recovery of the natural gas.

Optionally, the edge and bottom water invasion simulation apparatus includes a third intermediate container 17. A third piston 18 is disposed in the third intermediate container 17, and the third piston 18 is configured to separate natural gas and a liquid. A gas outlet end of the third intermediate container 17 is connected to the inlet end of the core holder 11, and the third intermediate container 17 is connected to the displacement pump 16 and the controller, respectively. The controller is further configured to set a corresponding pressure value of the displacement pump 16 to the initial formation pressure, so that the liquid enters the third intermediate container 17 from a liquid inlet end of the third intermediate container 17 to compress the natural gas inside the third intermediate container, so as to make an internal pressure of the third intermediate container 17 reach the initial formation pressure. The controller is further configured to control the natural gas in the third intermediate container 17 to be injected into the core in vacuum in the core holder 11, and to stop the natural gas from being injected into the core saturated with the natural gas in the core holder 11 when both the pressure at the outlet end of the core holder 11 and the pressure at the inlet end of the core holder 11 reach the initial formation pressure. The controller is further configured to determine the total volume of the natural gas in the core saturated with the natural gas according to the initial formation pressure, a gas deviation factor of the natural gas, atmospheric pressure, and a pore volume of the core.

In this embodiment, the edge and bottom water invasion simulation apparatus includes the third intermediate container 17. The third piston is disposed in the third intermediate container 17, and the third piston 18 is configured to separate the natural gas and the liquid. The gas outlet end of the third intermediate container 17 is connected to the inlet end of the core holder 11, and the third intermediate container 17 is connected to the displacement pump 16 and the controller, respectively.

The third intermediate container 17 includes a gas inlet end, the gas outlet end, the liquid inlet end and a liquid outlet end. The gas inlet end of the third intermediate container 17 is connected to a natural gas storage tank, and the gas outlet end of the third intermediate container 17 is connected to the inlet end of the core holder 11. The gas outlet end of the third intermediate container 17 may further be connected to a natural gas storage tank or a waste gas tank. The liquid inlet end of the third intermediate container 17 is connected to a liquid storage tank, and the liquid outlet end of the third intermediate container 17 is connected to a liquid storage tank or a waste liquid tank. The displacement pump 16 can introduce a liquid contained in the liquid storage tank into the third intermediate container 17. Specifically, the controller is further configured to control the displacement pump 16 to set the displacement pump 16 to be in a constant pressure mode, and the pressure value is the initial formation pressure, so that the liquid enters the third intermediate container 17 from the liquid inlet end of the third intermediate container 17. The liquid enters the third intermediate container 17, and then pushes the third piston to move upward to compress the natural gas in an upper part of the third intermediate container 17, so that the internal pressure of the third intermediate container 17 reaches the initial formation pressure. When both the pressure at the inlet end of the core holder 11 and the pressure at the outlet end of the core holder 11 reach the initial formation pressure, the injection of the natural gas into the core holder 11 is stopped, and the core is the core saturated with the natural gas at this time. A volume of the natural gas in the core saturated with the natural gas is determined according to the initial formation pressure, the pore volume of the core, the gas deviation factor of the natural gas, and the atmospheric pressure.

It should be noted that before the natural gas is injected into the core, the core needs to be subjected to a vacuum treatment. Specifically, the edge and bottom water invasion simulation apparatus further includes a vacuum pump. The vacuum pump is connected to an end of the core holder, and the vacuum pump is further connected to the controller. The controller controls the vacuum pump to be turned on to vacuumize the core.

Embodiment 3

Figure 3:
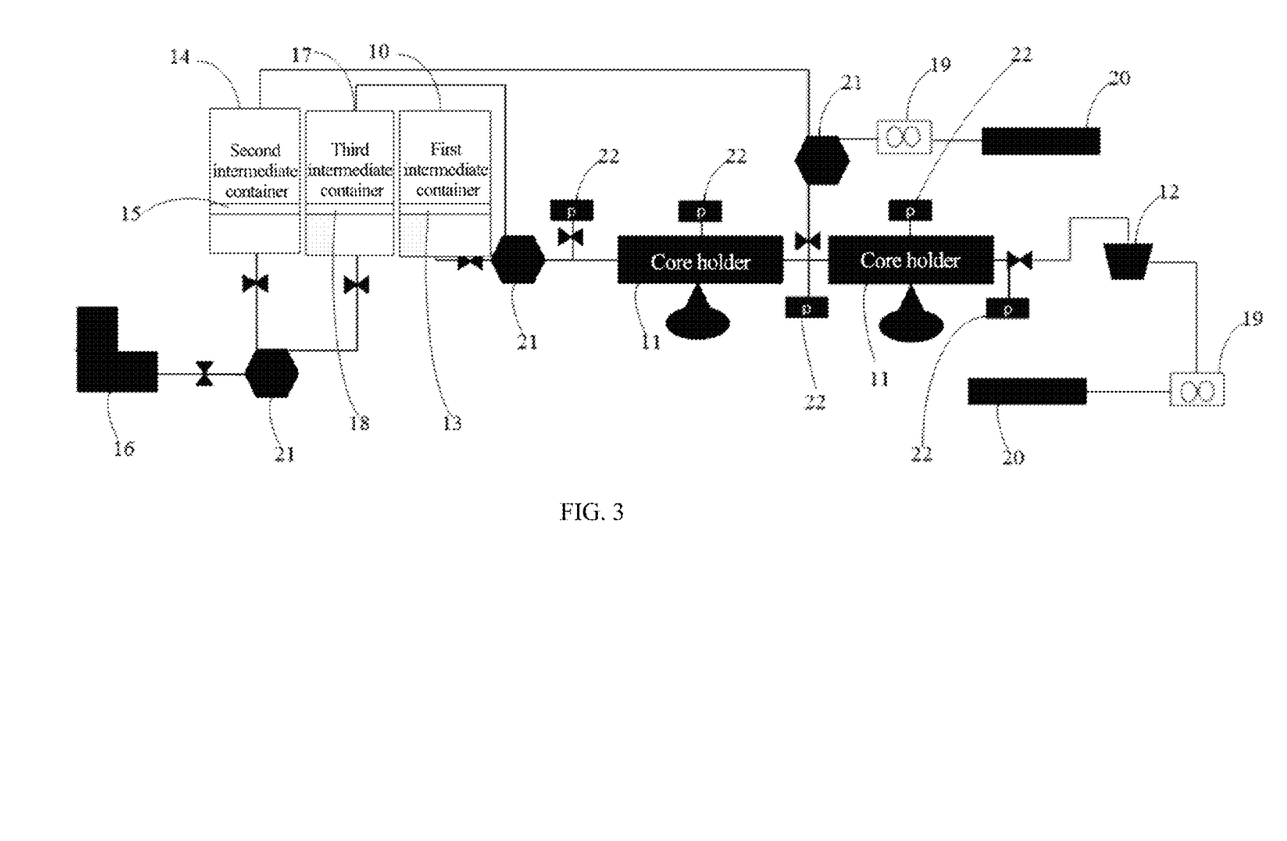
FIG. 3 is a schematic structural diagram of an edge and bottom water invasion simulation apparatus according to Embodiment 3 of the present disclosure.

FIG. 3 is a schematic structural diagram of an edge and bottom water invasion simulation apparatus according to Embodiment 3 of the present disclosure.

The edge and bottom water invasion simulation apparatus according to the present disclosure includes the first intermediate container, the core holder 11, the back pressure valve 12, and the controller. The first piston 13 is disposed in the first intermediate container, and the first piston 13 is configured to separate the formation water and the inert gas. The liquid outlet end of the first intermediate container is connected to the inlet end of the core holder 11, and the outlet end of the core holder 11 is connected to the back pressure valve 12. The controller is connected to the first intermediate container, the core holder 11, and the back pressure valve 12, respectively. Further, the edge and bottom water invasion simulation apparatus further includes the second intermediate container 14, the displacement pump 16, and the recovery device. The second piston 15 is disposed in the second intermediate container 14, and the second piston 15 is configured to separate the inert gas and the liquid. The second intermediate container 14 is connected to the displacement pump 16. The gas outlet end of the second intermediate container 14 is connected to the outlet end of the core holder 11, and the outlet end of the core holder 11 is connected to the recovery device. The controller is connected to the second intermediate container 14, the displacement pump 16, and the recovery device, respectively. The edge and bottom water invasion simulation apparatus further includes the third intermediate container 17. The third piston 18 is disposed in the third intermediate container 17, and the third piston 18 is configured to separate the natural gas and the liquid. The gas outlet end of the third intermediate container 17 is connected to the inlet end of the core holder 11, and the third intermediate container 17 is connected to the displacement pump 16 and the controller, respectively.

As shown in FIG. 3, the edge and bottom water invasion simulation apparatus is different from the edge and bottom water invasion simulation apparatus in the Embodiment 2. The edge and bottom water invasion simulation apparatus includes two core holders. One of the core holders is connected to the back pressure valve 12, the back pressure valve 12 is connected to the gas-liquid separator 19, and the gas-liquid separator 19 is connected to the gas flow meter 20. The outlet end of another core holder is connected to the gas-liquid separator 19, and the gas-liquid separator is connected to the gas flow meter 20. The two core holders are connected to each other. When the outlet end of one of the core holders is subjected to a water breakthrough, the controller controls the inert gas to be injected into the core holder that is subjected to the water breakthrough, and the controller uses another core holder that is not subjected to a water breakthrough to perform the exploitation, thereby simulating a multi-well exploitation mode in the actual exploitation.

Embodiment 4

Figure 4:
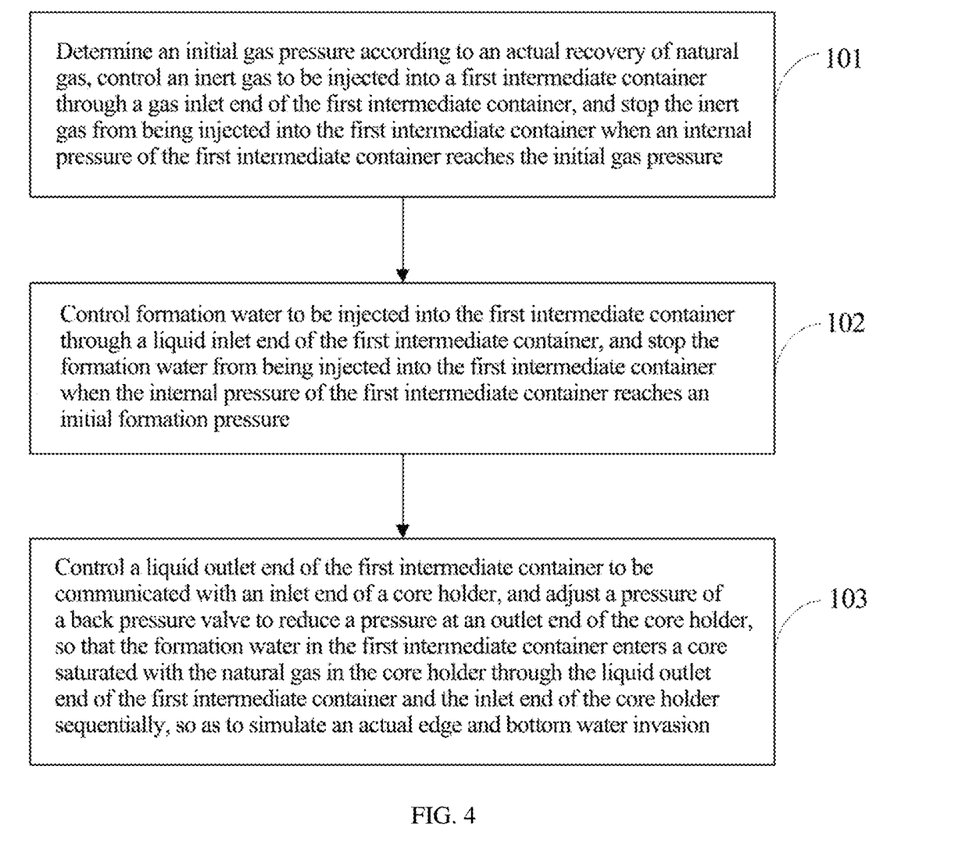
FIG. 4 is a schematic flowchart of an edge and bottom water invasion simulation method according to Embodiment 4 of the present disclosure.

FIG. 4 is a schematic flowchart of an edge and bottom water invasion simulation method according to Embodiment 4 of the present disclosure. An execution subject of the edge and bottom water invasion simulation method is an edge and bottom water invasion simulation apparatus, and the edge and bottom water invasion simulation apparatus is located in an electronic equipment. As shown in FIG. 4, the edge and bottom water invasion simulation method according to this embodiment includes following steps.

Step 101, determine an initial gas pressure according to an actual recovery of natural gas, control an inert gas to be injected into a first intermediate container through a gas inlet end of the first intermediate container, and stop the inert gas from being injected into the first intermediate container when an internal pressure of the first intermediate container reaches the initial gas pressure.

The execution subject in this embodiment is the edge and bottom water invasion simulation apparatus. The edge and bottom water invasion simulation apparatus includes the first intermediate container, a core holder, a back pressure valve, and a controller. The first intermediate container is a piston-type intermediate container, and is provided with a first piston therein. The first piston is configured to separate the inert gas and formation water. The first piston can move up and down in the first intermediate container when it is extruded. The first intermediate container includes the gas inlet end, a gas outlet end, a liquid inlet end, and a liquid outlet end. The gas inlet end of the first intermediate container is connected to an inert gas storage tank, and the gas outlet end of the first intermediate container is connected to an inert gas storage tank or a waste gas tank. The liquid inlet end of the first intermediate container is connected to a formation water storage tank, and the liquid outlet end of the first intermediate container is connected to an inlet end of the core holder. An outlet end of the core holder is connected to the back pressure valve, and the controller is connected to the first intermediate container, the core holder, and the back pressure valve, respectively.

In this embodiment, the initial gas pressure is firstly determined, and the initial gas pressure is determined according to the actual recovery of the natural gas. The inert gas in the inert gas storage tank is controlled to enter an upper part of the first intermediate container through the gas inlet end of the first intermediate container, and the internal pressure of the first intermediate container is detected. When the internal pressure of the first intermediate container reaches the initial gas pressure, the injection of the inert gas into the first intermediate container is stopped.

Step 102, control the formation water to be injected into the first intermediate container through the liquid inlet end of the first intermediate container, and stop the formation water from being injected into the first intermediate container when the internal pressure of the first intermediate container reaches an initial formation pressure.

In this embodiment, the formation water is injected into the first intermediate container, and the formation water in the formation water storage tank is further controlled to enter a lower part of the first intermediate container through the liquid inlet end of the first intermediate container. The formation water enters the first intermediate container, and then pushes the first piston to move upward to compress the inert gas in the upper part of the first intermediate container. The internal pressure of the first intermediate container is detected, and the injection of the formation water into the first intermediate container is stopped when the internal pressure of the first intermediate container reaches the initial formation pressure. The initial formation pressure can be set according to actual situations of a gas reservoir. During the actual natural gas production, the initial formation pressure will be measured in advance. In order to restore the actual reservoir environment, the initial formation pressure can be set to the corresponding initial formation pressure. The initial formation pressure can also be set according to user needs. In actual natural gas exploitation, an initial formation pressure during non-exploitation will be measured in advance. In order to restore an actual exploitation environment, the initial formation pressure can be set to the corresponding initial formation pressure during non-exploitation of the formation. The initial formation pressure can also be set according to user's needs.

Step 103, control the liquid outlet end of the first intermediate container to be communicated with the inlet end of the core holder, and adjust a pressure of the back pressure valve to reduce a pressure at the outlet end of the core holder, so that the formation water in the first intermediate container enters a core saturated with the natural gas in the core holder through the liquid outlet end of the first intermediate container and the inlet end of the core holder sequentially, so as to simulate an actual edge and bottom water invasion.

In this embodiment, the liquid outlet end of the first intermediate container is controlled to be communicated with the inlet end of the core holder. At this time, the core in the core holder is in a saturated state, that is, the core is the core saturated with the natural gas. The internal pressure of the core holder is the initial formation pressure, that is, the internal pressure of the core holder is equal to the internal pressure of the first intermediate container at this time. Further, the pressure of the back pressure valve is adjusted to reduce the pressure at the outlet end of the core holder, and the pressure at the outlet end of the core holder is lower than the internal pressure of the core holder, so that the natural gas in the core flows out from the outlet end of the core holder, and a reduction in the internal pressure of the core holder causes the formation water in the first intermediate container to enter the core in the core holder through the liquid outlet end of the first intermediate container and the inlet end of the core holder sequentially, thereby simulating the edge and bottom water invasion. As the formation water in the first intermediate container flows out, the internal pressure of the first intermediate container is reduced, so that the inert gas in the upper part of the first intermediate container expands. According to the principle of gas decompression and expansion, an expansion volume of the inert gas in the upper part of the first intermediate container is equal to a discharge volume of the formation water in the lower part. By combining with equation of state of gas and core parameters, a water invasion volume in the core can be quantitatively controlled, so that water breakthrough time of the outlet end of the core holder and a recovery of the natural gas during the water breakthrough are consistent with those in the actual exploitation, thereby accurately simulating the actual exploitation process. By adding the inert gas and the formation water to the first intermediate container, the infinite edge and bottom water with sufficient energy at the early stage of the water invasion and the limited edge and bottom water with lower energy at the later stage of the water invasion can be effectively simulated.

Embodiment 5

On the basis of the edge and bottom water invasion simulation method according to Embodiment 4 of the present disclosure, determining the initial gas pressure according to the actual recovery of the natural gas in Step 101 is further refined, and includes following steps.

Step 1011, calculate the initial gas pressure by substituting the actual recovery of the natural gas, a volume of the first intermediate container, an actual formation pressure corresponding to a water breakthrough of a gas reservoir, the initial formation pressure, a first gas deviation factor corresponding to the initial gas pressure, a second gas deviation factor corresponding to the actual formation pressure, a third gas deviation factor corresponding to the initial formation pressure, and a pore volume of the core into a formula, the formula being expressed as:

$$P_g = \frac{iV_s Z_g}{V_g \left(\frac{Z_1}{P_1} - \frac{Z_2}{P_2}\right)} \quad \text{Formula (1)}$$

where $P_g$ is the initial gas pressure, $i$ is the actual recovery of the natural gas, $V_s$ is the pore volume of the core, $Z_g$ is the first gas deviation factor, $V_g$ is the volume of the first intermediate container, $Z_1$ is the second gas deviation factor, $Z_2$ is the third gas deviation factor, $P_1$ is the actual formation pressure, and $P_2$ is the initial formation pressure.

In this embodiment, the actual recovery of the natural gas, the volume of the first intermediate container, the actual formation pressure corresponding to the water breakthrough of the gas reservoir, the initial formation pressure, the first gas deviation factor corresponding to the initial gas pressure, and the second gas deviation factor corresponding to the actual formation pressure, the third gas deviation factor corresponding to the initial formation pressure, and the pore volume of the core are obtained. The actual recovery of the natural gas, the volume of the first intermediate container, the actual formation pressure corresponding to the water breakthrough of the gas reservoir, the initial formation pressure, the first gas deviation factor corresponding to the initial gas pressure, and the second gas deviation factor corresponding to the actual formation pressure, the third gas deviation factor corresponding to the initial formation pressure, and the pore volume of the core are substituted into Formula (1) to calculate the initial gas pressure.

It should be noted that among the above parameters, the actual recovery of the natural gas, the volume of the first intermediate container, the actual formation pressure corresponding to the water breakthrough of the gas reservoir, the initial formation pressure, the first gas deviation factor corresponding to the initial gas pressure, and the second gas deviation factor corresponding to the actual formation pressure, and the third gas deviation factor corresponding to the initial formation pressure are known, and the pore volume of the core is unknown, which can be calculated.

A calculation method of the pore volume of the core is as follows: drying the core, putting the dried core into the core holder, vacuumizing, connecting the core holder to a gas cylinder containing an inert gas, injecting the inert gas into the core holder to enable the inert gas to freely diffuse in the core, regarding as a system balance when an internal pressure of the gas cylinder and an internal pressure of the core are equal, considering that an initial pressure of the gas cylinder, an equilibrium pressure of the system, a volume of the core, and an initial volume of the inert gas in the gas cylinder are known, substituting the foregoing parameters into Formula (2) to calculate the pore volume of the core, and Formula (2) being as follows:

$$V_0 = \frac{Z_2 P_1 V_1}{Z_1 P_2} - V_1 - V_2 \quad \text{Formula (2)}$$

where $V_0$ is the pore volume of the core, $Z_2$ is a gas deviation factor of the inert gas under the equilibrium pressure of the system, $P_1$ is the initial pressure of the gas cylinder, $V_1$ is the initial volume of the inert gas in the gas cylinder, $Z_1$ is a gas deviation factor of the inert gas under the initial pressure of the gas cylinder, $P_2$ is the equilibrium pressure of the system, and $V_2$ is a pore volume between a pipe and a port at any end of the core holder.

Embodiment 6

On the basis of the edge and bottom water invasion simulation method according to Embodiment 4 of the present disclosure, after Step 103, further including following steps.

Step 1031, control the outlet end of the core holder to be disconnected from a recovery device when the outlet end of the core holder is subjected to a first water breakthrough.

The edge and bottom water invasion simulation apparatus further includes a second intermediate container, a displacement pump, and the recovery device. A second piston is disposed in the second intermediate container, and the second piston is configured to separate an inert gas and a liquid. The second intermediate container is connected to the displacement pump, a gas outlet end of the second intermediate container is connected to the outlet end of the core holder, and the outlet end of the core holder is connected to the recovery device. The controller is connected to the second intermediate container, the displacement pump, and the recovery device, respectively.

In this embodiment, when the outlet end of the core holder is subjected to the first water breakthrough, since the outlet end of the core holder no longer produces gas, the outlet end of the core holder is controlled to be disconnected from the recovery device, and the recovery is stopped. There is still remaining natural gas in the core that has not been produced. Further, the inert gas can be used to push the formation water in, and then the recovery is performed.

Optionally, in order to determine how much inert gas is most suitable for injection in actual use, different injection volumes of the inert gas can be set, and the recovery is calculated after the inert gas is injected, so as to obtain a relationship between the injection volume of the inert gas and the recovery of the natural gas, and to determine the injection volume of the inert gas during the first water breakthrough in actual exploitation from the cost, the recovery and other aspects.

Step 1032, set a corresponding pressure value of a displacement pump to the initial formation pressure, so that a liquid enters a second intermediate container from a liquid inlet end of the second intermediate container to compress the inert gas inside the second intermediate container, so as to make an internal pressure of the second intermediate container reach the initial formation pressure.

In this embodiment, the displacement pump is set to be in a constant pressure mode, and a pressure value is the initial formation pressure, so that the liquid contained in a liquid storage tank is introduced into the second intermediate container. The liquid enters the second intermediate container, and then pushes the second piston to move upward to compress the inert gas in an upper part of the second intermediate container, so that the internal pressure of the second intermediate container reaches the initial formation pressure. According to a liquid intake amount of the liquid entering the second intermediate container and a volume of the second intermediate container, a volume of the inert gas of high pressure can be calculated.

Step 1033, when the internal pressure of the second intermediate container reaches the initial formation pressure, control the outlet end of the core holder to be communicated with a gas outlet end of the second intermediate container, so that the inert gas in the second intermediate container enters the core holder through the gas outlet end of the second intermediate container and the outlet end of the core holder sequentially, and determine an injection volume of the inert gas entering the core holder according to a liquid injection volume when an internal pressure of the core holder reaches the initial formation pressure.

In this embodiment, after the internal pressure of the second intermediate container reaches the initial formation pressure, the controller controls the outlet end of the core holder to be communicated with the gas outlet end of the second intermediate container. Since the pressure at the outlet end of the core holder is less than the internal pressure of the second intermediate container, the inert gas in the second intermediate container enters the core holder through the gas outlet end of the second intermediate container and the outlet end of the core holder sequentially. Until the internal pressure of the core holder reaches the initial formation pressure, the injection of the inert gas into the core holder is stopped. At this time, a liquid intake amount of the displacement pump is obtained, and the liquid intake amount of the displacement pump is equal to the injection volume of the inert gas injected into the core holder.

Step 1034, when the internal pressure of the core holder is the initial formation pressure, control the outlet end of the core holder to be communicated with the recovery device, and adjust the pressure of the back pressure valve to reduce the pressure at the outlet end of the core holder, so that a gas inside the core holder flows from the outlet end into the recovery device.

In this embodiment, when the internal pressure of the core holder reaches the initial formation pressure, the recovery can be performed at this time, and the controller controls the outlet end of the core holder to be communicated with the recovery device. Further, a gas is discharged from the outlet end of the core holder, and the gas includes the inert gas and the natural gas.

Step 1035, when the outlet end of the core holder is subjected to a second water breakthrough, control the outlet end of the core holder to be disconnected from the recovery device, and analyze a gas recovered by the recovery device to determine a recovery volume of the natural gas, and determine a recovery of the natural gas during the second water breakthrough according to the recovery volume of the natural gas and a total volume of the natural gas in a core saturated with the natural gas.

In this embodiment, when the outlet end of the core holder is subjected to the second water breakthrough, the outlet end of the core holder is controlled to be disconnected from the recovery device, and the recovery is not performed. A gas chromatograph is used to analyze the gas recovered by the recovery device, so as to determine the recovery volume of the natural gas. The recovery of the natural gas during the second water breakthrough is determined according to the recovery volume of the natural gas and the total volume of the natural gas in the core saturated with the natural gas. Specifically, a ratio of the recovery volume of the natural gas to the total volume of the natural gas in the core saturated with the natural gas is calculated, and the ratio is determined as the recovery of the natural gas.

Embodiment 7

Figure 5:
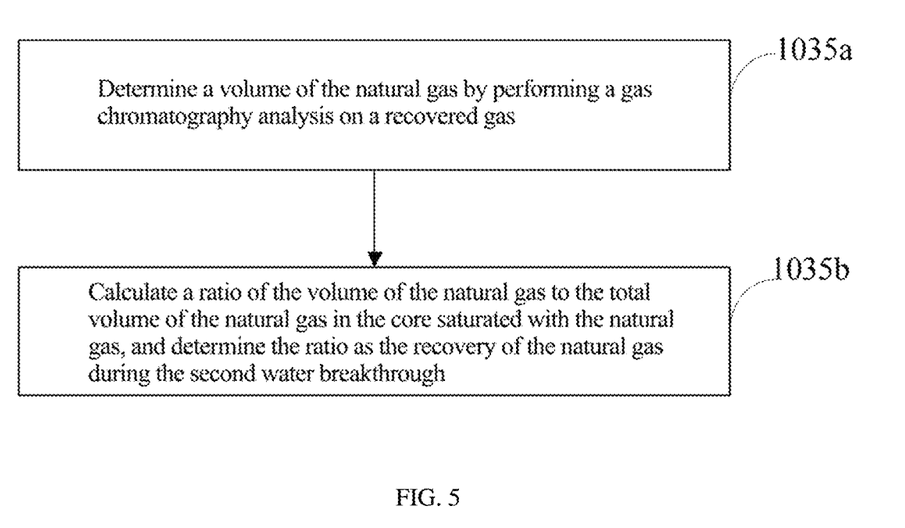
FIG. 5 is a schematic flowchart of an edge and bottom water invasion simulation method according to Embodiment 7 of the present disclosure.

FIG. 5 is a schematic flowchart of an edge and bottom water invasion simulation method according to Embodiment 7 of the present disclosure. As shown in FIG. 5, determining the recovery of the natural gas during the second water breakthrough according to the recovery volume of the natural gas and the total volume of the natural gas in the core saturated with the natural gas in Step 1035 is refined, and includes following steps.

Step 1035a, determine a volume of the natural gas by performing a gas chromatography analysis on a recovered gas.

In this embodiment, the recovered gas includes the inert gas and the natural gas. The recovered gas is analyzed by using the gas chromatograph, so as to obtain a volume of the inert gas, the volume of the natural gas, and proportions of the two gases in a gas total volume.

Step 1035b, calculate a ratio of the volume of the natural gas to the total volume of the natural gas in the core saturated with the natural gas, and determine the ratio as the recovery of the natural gas during the second water breakthrough.

In this embodiment, the ratio of the volume of natural gas to the total volume of the natural gas in the core saturated with the natural gas is calculated, and the obtained ratio is the recovery of the natural gas during the second water breakthrough.

Embodiment 8

Figure 6:
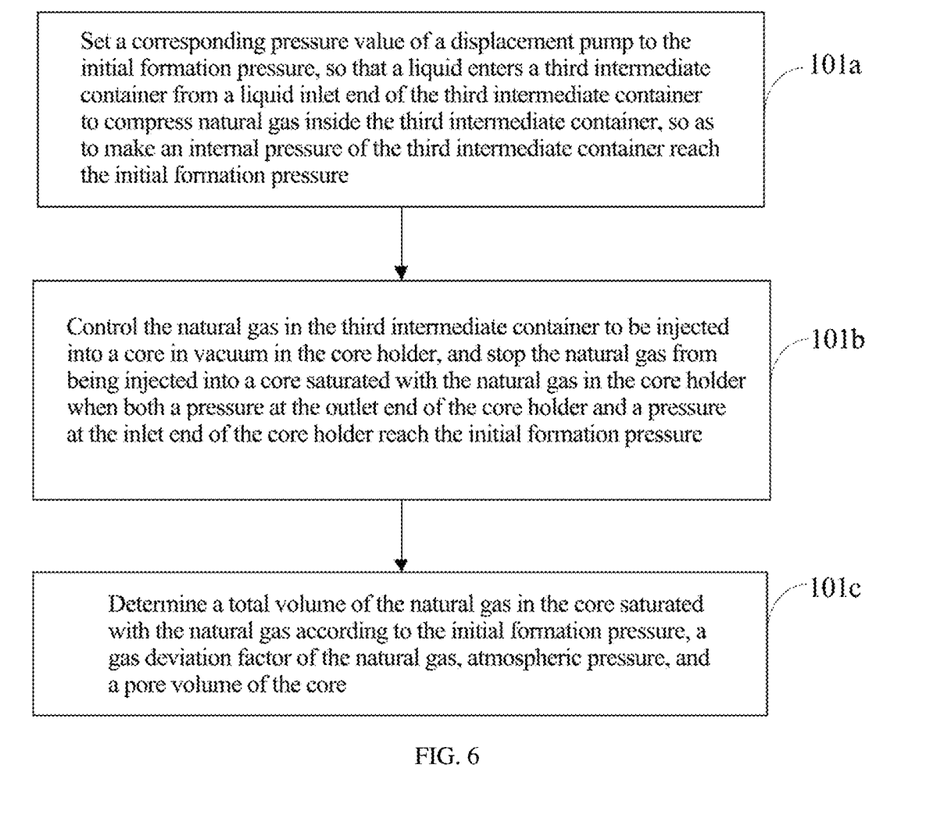
FIG. 6 is a schematic flowchart of an edge and bottom water invasion simulation method according to Embodiment 8 of the present disclosure.

FIG. 6 is a schematic flowchart of an edge and bottom water invasion simulation method according to Embodiment 8 of the present disclosure. As shown in FIG. 6, before Step 101, further including following steps.

101a, set a corresponding pressure value of the displacement pump to the initial formation pressure, so that a liquid enters a third intermediate container from a liquid inlet end of the third intermediate container to compress natural gas inside the third intermediate container, so as to make an internal pressure of the third intermediate container reach the initial formation pressure.

In this embodiment, the edge and bottom water invasion simulation apparatus includes the third intermediate container. A third piston is disposed in the third intermediate container, and the third piston is configured to separate the natural gas and the liquid. A gas outlet end of the third intermediate container is connected to the inlet end of the core holder. The third intermediate container is connected to the displacement pump and the controller, respectively.

In this embodiment, the displacement pump is set to be in a constant pressure mode, and the pressure value is the initial formation pressure, so that the liquid enters the third intermediate container from the liquid inlet end of the third intermediate container. The liquid enters the third intermediate container, and then pushes the third piston to move upward to compress the natural gas in an upper part of the third intermediate container, so that the internal pressure of the third intermediate container reaches the initial formation pressure.

101b, control the natural gas in the third intermediate container to be injected into a core in vacuum in the core holder, and stop the natural gas from being injected into a core saturated with the natural gas in the core holder when both a pressure at the outlet end of the core holder and a pressure at the inlet end of the core holder reach the initial formation pressure.

In this embodiment, when both the pressure at the inlet end of the core holder and the pressure at the outlet end of the core holder reach the initial formation pressure, the injection of the natural gas into the core holder is stopped, and the core is the core saturated with the natural gas at this time. A volume of the natural gas in the core saturated with the natural gas is determined according to the initial formation pressure, a pore volume of the core, a gas deviation factor of the natural gas, and atmospheric pressure.

101c, determine a total volume of the natural gas in the core saturated with the natural gas according to the initial formation pressure, the gas deviation factor of the natural gas, the atmospheric pressure, and the pore volume of the core.

In this embodiment, the volume of the natural gas in the core saturated with the natural gas is determined according to the initial formation pressure, the pore volume of the core, the gas deviation factor of the natural gas, and the atmospheric pressure, and the volume of the natural gas in the core saturated with the natural gas is calculated by substituting the above parameters into Formula (3):

$$V_g = \frac{Z_0 P_1 V_0}{Z_1 P_0} \quad \text{Formula (3)}$$

where $V_g$ is the volume of the natural gas in the core saturated with the natural gas, $Z_0$ is the gas deviation factor of the natural gas under the atmospheric pressure, $P_1$ is a corresponding pressure when the pressures at the outlet end and the inlet end of the core holder are equal, $V_0$ is the pore volume of the core, $Z_1$ is the gas deviation factor of the natural gas when the pressures at the outlet end and the inlet end of the core holder are equal, and $P_0$ is the atmospheric pressure.

Those skilled in the art will easily conceive of other embodiments of the present disclosure after considering the specification and practicing the invention disclosed herein. The present invention is intended to include any variations, uses, or adaptive changes of the present disclosure. These variations, uses, or adaptive changes follow the general principles of the present disclosure, and include common knowledge or conventional technical means in the art that are not disclosed in the present disclosure. The description and the embodiments are only regarded to be exemplary, and the true scope and spirit of the present disclosure are pointed out by the following claims.

It should be understood that the present disclosure is not limited to the precise structure that has been described above and shown in the drawings, and various modifications and changes can be made without departing from its scope. The scope of the present disclosure is only limited by the appended claims.

What is claimed is:

1. An edge and bottom water invasion simulation apparatus, wherein the apparatus comprises a first intermediate container, a core holder, a back pressure valve, and a controller, wherein a first piston is disposed in the first intermediate container, and the first piston is configured to separate formation water and an inert gas; a liquid outlet end of the first intermediate container is connected to an inlet end of the core holder, and an outlet end of the core holder is connected to the back pressure valve; the controller is connected to the first intermediate container, the core holder, and the back pressure valve, respectively;

the controller is configured to control the inert gas to be injected into the first intermediate container through a gas inlet end of the first intermediate container, and to stop the inert gas from being injected into the first intermediate container when an internal pressure of the first intermediate container reaches an initial gas pressure;

the controller is configured to control the formation water to be injected into the first intermediate container through a liquid inlet end of the first intermediate container, and to stop the formation water from being injected into the first intermediate container when the internal pressure of the first intermediate container reaches an initial formation pressure;

the controller is configured to control the liquid outlet end of the first intermediate container to be communicated with the inlet end of the core holder;

the controller is configured to adjust a pressure of the back pressure valve to reduce a pressure at the outlet end of the core holder, so that the formation water in the first intermediate container enters a core in the core holder through the liquid outlet end of the first intermediate container and the inlet end of the core holder sequentially, so as to simulate an edge and bottom water invasion;

wherein the apparatus further comprises a second intermediate container, a displacement pump, and a recovery device, a second piston is disposed in the second intermediate container, and the second piston is configured to separate an inert gas and a liquid; the second intermediate container is connected to the displacement pump, a gas outlet end of the second intermediate container is connected to the outlet end of the core holder, and the outlet end of the core holder is connected to the recovery device; the controller is connected to the second intermediate container, the displacement pump, and the recovery device, respectively;

the controller is further configured to control the outlet end of the core holder to be disconnected from the recovery device when the outlet end of the core holder is subjected to a first water breakthrough;

the controller is further configured to set a corresponding pressure value of the displacement pump to the initial formation pressure, so that the liquid enters the second intermediate container from a liquid inlet end of the second intermediate container to compress the inert gas in the second intermediate container, so as to make an internal pressure of the second intermediate container reach the initial formation pressure;

the controller is further configured to, when the internal pressure of the second intermediate container reaches the initial formation pressure, control the outlet end of the core holder to be communicated with the gas outlet end of the second intermediate container, so that the inert gas in the second intermediate container enters the core holder through the gas outlet end of the second intermediate container and the outlet end of the core holder sequentially;

the controller is further configured to determine an injection volume of the inert gas entering the core holder according to a liquid injection volume when an internal pressure of the core holder reaches the initial formation pressure;

the controller is further configured to, when the internal pressure of the core holder reaches the initial formation pressure, control the outlet end of the core holder to be communicated with the recovery device, and adjust the pressure of the back pressure valve to reduce the pressure at the outlet end of the core holder, so that a gas inside the core holder flows from the outlet end of the core holder into the recovery device;

the controller is further configured to, when the outlet end of the core holder is subjected to a second water breakthrough, control the outlet end of the core holder to be disconnected from the recovery device, and analyze the gas recovered by the recovery device to determine a recovery volume of natural gas, and determine a recovery of the natural gas during the second water breakthrough according to the recovery volume of the natural gas and a total volume of the natural gas in the core saturated with the natural gas.

2. The apparatus according to claim 1, wherein the apparatus comprises a third intermediate container, a third piston is disposed in the third intermediate container, and the third piston is configured to separate natural gas and a liquid; a gas outlet end of the third intermediate container is connected to the inlet end of the core holder, and the third intermediate container is connected to the displacement pump and the controller, respectively;

the controller is further configured to set a corresponding pressure value of the displacement pump to the initial formation pressure, so that the liquid enters the third intermediate container from a liquid inlet end of the third intermediate container to compress the natural gas inside the third intermediate container, so as to make an internal pressure of the third intermediate container reach the initial formation pressure;

the controller is further configured to control the natural gas in the third intermediate container to be injected into the core in vacuum in the core holder, and to stop the natural gas from being injected into the core saturated with the natural gas in the core holder when both a pressure at the outlet end of the core holder and a pressure at the inlet end of the core holder reach the initial formation pressure;

the controller is further configured to determine the total volume of the natural gas in the core saturated with the natural gas according to the initial formation pressure, a gas deviation factor of the natural gas, atmospheric pressure, and a pore volume of the core.

3. An edge and bottom water invasion simulation method, wherein the method comprises:

determining an initial gas pressure according to an actual recovery of natural gas, controlling an inert gas to be injected into a first intermediate container through a gas inlet end of the first intermediate container, and stopping the inert gas from being injected into the first intermediate container when an internal pressure of the first intermediate container reaches the initial gas pressure;

controlling formation water to be injected into the first intermediate container through a liquid inlet end of the first intermediate container, and stopping the formation water from being injected into the first intermediate container when the internal pressure of the first intermediate container reaches an initial formation pressure; and controlling a liquid outlet end of the first intermediate container to be communicated with an inlet end of a core holder, and adjusting a pressure of a back pressure valve to reduce a pressure at an outlet end of the core holder, so that the formation water in the first intermediate container enters a core saturated with the natural gas in the core holder through the liquid outlet end of the first intermediate container and the inlet end of the core holder sequentially, so as to simulate an actual edge and bottom water invasion;

wherein after the adjusting the pressure of the back pressure valve to reduce the pressure at the outlet end of the core holder, the method further comprises:

controlling the outlet end of the core holder to be disconnected from a recovery device when the outlet end of the core holder is subjected to a first water breakthrough;

setting a corresponding pressure value of a displacement pump to the initial formation pressure, so that a liquid enters a second intermediate container from a liquid inlet end of the second intermediate container to compress an inert gas inside the second intermediate container, so as to make an internal pressure of the second intermediate container reach the initial formation pressure;

when the internal pressure of the second intermediate container reaches the initial formation pressure, controlling the outlet end of the core holder to be communicated with a gas outlet end of the second intermediate container, so that the inert gas in the second intermediate container enters the core holder through the gas outlet end of the second intermediate container and the outlet end of the core holder sequentially, and determining an injection volume of the inert gas entering the core holder according to a liquid injection volume when an internal pressure of the core holder reaches the initial formation pressure;

when the internal pressure of the core holder is the initial formation pressure, controlling the outlet end of the core holder to be communicated with the recovery device, and adjusting the pressure of the back pressure valve to reduce the pressure at the outlet end of the core holder, so that a gas inside the core holder flows from the outlet end into the recovery device; and when the outlet end of the core holder is subjected to a second water breakthrough, controlling the outlet end of the core holder to be disconnected from the recovery device, and analyzing a gas recovered by the recovery device to determine a recovery volume of the natural gas, and determining a recovery of the natural gas during the second water breakthrough according to the recovery volume of the natural gas and a total volume of the natural gas in a core saturated with the natural gas.

4. The method according to claim 3, wherein the determining the initial gas pressure according to the actual recovery of the natural gas comprises:

calculating the initial gas pressure by substituting the actual recovery of the natural gas, a volume of the first intermediate container, a corresponding actual formation pressure when a gas reservoir is subjected to a water breakthrough, the initial formation pressure, a first gas deviation factor corresponding to the initial gas pressure, a second gas deviation factor corresponding to the actual formation pressure, a third gas deviation factor corresponding to the initial formation pressure, and a pore volume of the core into a formula, the formula being expressed as:

$$P_g = \frac{iV_s Z_g}{V_g \left(\frac{Z_1}{P_1} - \frac{Z_2}{P_2}\right)}$$

wherein $P_g$ is the initial gas pressure, i is the actual recovery of the natural gas, $V_s$ is the pore volume of the core, $Z_g$ is the first gas deviation factor, $V_g$ is the volume of the first intermediate container, $Z_1$ is the second gas deviation factor, $Z_2$ is the third gas deviation factor, $P_1$ is the actual formation pressure, and $P_2$ is the initial formation pressure.

5. The method according to claim 3, wherein the determining the recovery of the natural gas during the second water breakthrough according to the recovery volume of the natural gas and the total volume of the natural gas in the core saturated with the natural gas comprises:

determining a volume of the natural gas by performing a gas chromatography analysis on a recovered gas;

calculating a ratio of the volume of the natural gas to the total volume of the natural gas in the core saturated with the natural gas, and determining the ratio as the recovery of the natural gas during the second water breakthrough.

6. The method according to claim 3, wherein before the determining the initial gas pressure according to the actual recovery of the natural gas, the method further comprises:

setting a corresponding pressure value of a displacement pump to the initial formation pressure, so that a liquid enters a third intermediate container from a liquid inlet end of the third intermediate container to compress natural gas inside the third intermediate container, so as to make an internal pressure of the third intermediate container reach the initial formation pressure;

controlling the natural gas in the third intermediate container to be injected into a core in vacuum in the core holder, and stopping the natural gas from being injected into a core saturated with the natural gas in the core holder when both a pressure at the outlet end of the core holder and a pressure at the inlet end of the core holder reach the initial formation pressure; and determining a total volume of the natural gas in the core saturated with the natural gas according to the initial formation pressure, a gas deviation factor of the natural gas, atmospheric pressure, and a pore volume of the core.

7. A computer program product comprising computer programs, wherein when a processor executes the computer programs, the method according to claim 3 is implemented.

8. A non-transitory computer-readable storage medium, wherein computer-executable instructions are stored in the computer-readable storage medium, and when a processor executes the computer-executable instructions, the processor is enabled to:

determine an initial gas pressure according to an actual recovery of natural gas, control an inert gas to be injected into a first intermediate container through a gas inlet end of the first intermediate container, and stop the inert gas from being injected into the first intermediate container when an internal pressure of the first intermediate container reaches the initial gas pressure;

control formation water to be injected into the first intermediate container through a liquid inlet end of the first intermediate container, and stop the formation water from being injected into the first intermediate container when the internal pressure of the first intermediate container reaches an initial formation pressure; and control a liquid outlet end of the first intermediate container to be communicated with an inlet end of a core holder, and adjust a pressure of a back pressure valve to reduce a pressure at an outlet end of the core holder, so that the formation water in the first intermediate container enters a core saturated with the natural gas in the core holder through the liquid outlet end of the first intermediate container and the inlet end of the core holder sequentially, so as to simulate an actual edge and bottom water invasion;

control the outlet end of the core holder to be disconnected from a recovery device when the outlet end of the core holder is subjected to a first water breakthrough;

set a corresponding pressure value of a displacement pump to the initial formation pressure, so that a liquid enters a second intermediate container from a liquid inlet end of the second intermediate container to compress an inert gas inside the second intermediate container, so as to make an internal pressure of the second intermediate container reach the initial formation pressure;

when the internal pressure of the second intermediate container reaches the initial formation pressure, control the outlet end of the core holder to be communicated with a gas outlet end of the second intermediate container, so that the inert gas in the second intermediate container enters the core holder through the gas outlet end of the second intermediate container and the outlet end of the core holder sequentially, and determine an injection volume of the inert gas entering the core holder according to a liquid injection volume when an internal pressure of the core holder reaches the initial formation pressure;

when the internal pressure of the core holder is the initial formation pressure, control the outlet end of the core holder to be communicated with the recovery device, and adjust the pressure of the back pressure valve to reduce the pressure at the outlet end of the core holder, so that a gas inside the core holder flows from the outlet end into the recovery device; and when the outlet end of the core holder is subjected to a second water breakthrough, control the outlet end of the core holder to be disconnected from the recovery device, and analyze a gas recovered by the recovery device to determine a recovery volume of the natural gas, and determine a recovery of the natural gas during the second water breakthrough according to the recovery volume of the natural gas and a total volume of the natural gas in a core saturated with the natural gas.

9. The non-transitory computer-readable storage medium according to claim 8, wherein the processor is further enabled to:

calculate the initial gas pressure by substituting the actual recovery of the natural gas, a volume of the first intermediate container, an actual formation pressure corresponding to a water breakthrough of a gas reservoir, the initial formation pressure, a first gas deviation factor corresponding to the initial gas pressure, a second gas deviation factor corresponding to the actual formation pressure, a third gas deviation factor corresponding to the initial formation pressure, and a pore volume of the core into a formula, the formula being expressed as:

$$P_g = \frac{iV_s Z_g}{V_g \left(\frac{Z_1}{P_1} - \frac{Z_2}{P_2}\right)}$$

wherein $P_g$ is the initial gas pressure, i is the actual recovery of the natural gas, $V_s$ is the pore volume of the core, $Z_g$ is the first gas deviation factor, $V_g$ is the volume of the first intermediate container, $Z_1$ is the second gas deviation factor, $Z_2$ is the third gas deviation factor, $P_1$ is the actual formation pressure, and $P_2$ is the initial formation pressure.

10. The non-transitory computer-readable storage medium according to claim 8, wherein the processor is further enabled to:

determine a volume of the natural gas by performing a gas chromatography analysis on a recovered gas;

calculate a ratio of the volume of the natural gas to the total volume of the natural gas in the core saturated with the natural gas, and determine the ratio as the recovery of the natural gas during the second water breakthrough.

11. The non-transitory computer-readable storage medium according to claim 8, wherein before the determining the initial gas pressure according to the actual recovery of the natural gas, the processor is further enabled to:

set a corresponding pressure value of a displacement pump to the initial formation pressure, so that a liquid enters a third intermediate container from a liquid inlet end of the third intermediate container to compress natural gas inside the third intermediate container, so as to make an internal pressure of the third intermediate container reach the initial formation pressure;

control the natural gas in the third intermediate container to be injected into a core in vacuum in the core holder, and stop the natural gas from being injected into a core saturated with the natural gas in the core holder when both a pressure at the outlet end of the core holder and a pressure at the inlet end of the core holder reach the initial formation pressure; and determine a total volume of the natural gas in the core saturated with the natural gas according to the initial formation pressure, a gas deviation factor of the natural gas, atmospheric pressure, and a pore volume of the core.

* * * * *